(12) United States Patent
Tsukada et al.

(10) Patent No.: US 12,249,443 B2
(45) Date of Patent: Mar. 11, 2025

(54) ELASTIC WIRING AND METHOD FOR PRODUCING ELASTIC WIRING

(71) Applicant: NIPPON TELEGRAPH AND TELEPHONE CORPORATION, Tokyo (JP)

(72) Inventors: Shingo Tsukada, Atsugi (JP); Hiroshi Nakashima, Atsugi (JP)

( * ) Notice: Subject to any disclaimer, the term of this patent is extended or adjusted under 35 U.S.C. 154(b) by 0 days.

(21) Appl. No.: 18/645,562

(22) Filed: Apr. 25, 2024

(65) Prior Publication Data

US 2024/0296974 A1 Sep. 5, 2024

Related U.S. Application Data

(62) Division of application No. 16/758,256, filed as application No. PCT/JP2018/041969 on Nov. 13, 2018, now Pat. No. 11,996,216.

(30) Foreign Application Priority Data

Nov. 15, 2017 (JP) ................. 2017-220478

(51) Int. Cl.
| | |
|---|---|
| *H01B 7/282* | (2006.01) |
| *A41D 1/00* | (2018.01) |
| *A61B 5/00* | (2006.01) |
| *A61B 5/024* | (2006.01) |
| *A61B 5/25* | (2021.01) |
| *A61B 5/291* | (2021.01) |
| *H01B 7/04* | (2006.01) |

(Continued)

(52) U.S. Cl.
CPC ............ *H01B 7/282* (2013.01); *A41D 1/005* (2013.01); *A61B 5/02438* (2013.01); *A61B 5/6804* (2013.01); *H01B 7/04* (2013.01); *H02G 1/08* (2013.01)

(58) Field of Classification Search
CPC .. H01B 7/04; H01B 7/06; A41D 1/005; A61B 5/02438; A61B 5/6804; A61B 5/25; A61B 5/291

See application file for complete search history.

(56) References Cited

U.S. PATENT DOCUMENTS

| | | |
|---|---|---|
| 6,341,504 B1 | 1/2002 | Istook |
| 9,378,864 B1 | 6/2016 | Liu et al. |
| 11,610,701 B2 | 3/2023 | Tsukada et al. |

(Continued)

FOREIGN PATENT DOCUMENTS

| | | |
|---|---|---|
| CN | 2837581 Y | 11/2006 |
| JP | S57017007 U | 1/1982 |

(Continued)

OTHER PUBLICATIONS

Kazuhiko Takagahara et al., "hitoe"—A wearable Sensor Developed through Cross-industrial Collaboration, NTT Technical Journal, vol. 26, No. 5, pp. 42-44, May 1, 2014.

(Continued)

*Primary Examiner* — Timothy J Thompson
*Assistant Examiner* — Amol H Patel (57) ABSTRACT

An elastic wiring includes: an elastic tube; a conductor wire arranged within the tube; and fixing portions that fix the conductor wire and the tube at both ends of the tube in the lengthwise direction, wherein the length of the conductor wire between the fixing portions when the tube is in an unextended state is longer than the length of the tube between the fixing portions.

2 Claims, 6 Drawing Sheets

(51) Int. Cl.
*H01B 7/06* (2006.01)
*H02G 1/08* (2006.01)

(56) References Cited

U.S. PATENT DOCUMENTS

| | | | |
|---|---|---|---|
| 11,678,827 B2 | 6/2023 | Tsukada et al. | |
| 11,996,216 B2 | 5/2024 | Tsukada et al. | |
| 12,027,288 B2 | 7/2024 | Tsukada et al. | |
| 2006/0080808 A1 | 4/2006 | Bishop | |
| 2006/0185873 A1 | 8/2006 | Johnson | |
| 2014/0020928 A1 | 1/2014 | Johnson | |
| 2019/0018511 A1 | 1/2019 | Yoshida et al. | |

FOREIGN PATENT DOCUMENTS

| | | |
|---|---|---|
| JP | S59118228 U | 8/1984 |
| JP | S59130326 U | 9/1984 |
| JP | H05-043420 U | 6/1993 |
| JP | 2000194957 A | 7/2000 |
| JP | 2012227061 A | 11/2012 |
| JP | 2013018161 A | 1/2013 |
| JP | 2017050155 A | 3/2017 |
| JP | 2017121442 A | 7/2017 |
| JP | 2017140213 A | 8/2017 |
| WO | WO-2017110490 A1 | 6/2017 |

OTHER PUBLICATIONS

Matteo Stoppa et al., "Wearable Electronics and Smart Textiles: A Critical Review", Sensors, vol. 14, No. 7, pp. 11957-11992, 2014.
Japanese Office Action regarding corresponding application No. 2019-554225, dated Jun. 30, 2020. Translation attached.
Japanese Office Action from counterpart JP2020175611, mailed Oct. 5, 2021.
International Search Report (in English and Japanese) issued in International Application PCT/JP2018/041969, mailed Dec. 11, 2018; ISA/JP.

ELASTIC WIRING AND METHOD FOR PRODUCING ELASTIC WIRING

CROSS-REFERENCE TO RELATED APPLICATIONS

This application is a divisional of U.S. patent application Ser. No. 16/758,256, filed on Apr. 22, 2020 which is a 371 National Phase of International Application No. PCT/JP2018/041969, filed on Nov. 13, 2018, which claims priority to Japanese Application No. 2017-220478, filed on Nov. 15, 2017. The entire disclosures of the above applications are incorporated herein by reference.

TECHNICAL FIELD

The present invention relates to an elastic wiring and a method for producing an elastic wiring.

BACKGROUND ART

In for example a medical device, a health device, a physiological function testing device, or a research device that acquires an electrical biological signal such as an electrocardiograph or an electroencephalograph, the electrical signal is transmitted and received between a bioelectrode in contact with the living body and the device. For that reason, the bioelectrode and the device are connected by wiring (for example, Non-Patent Documents 1 and 2). When the wiring is placed in an unstable state at a position away from the body, noise due to body movement or wiring vibration is picked up and the signal-to-noise ratio (S/N ratio) tends to deteriorate. On the other hand, a body has a large capacitance, and so a shielding effect can be obtained in the vicinity of the body. Therefore, the portion of the wiring on the bioelectrode side is usually fixed along the surface of the body.

The wiring, due to generally lacking elasticity and being relatively rigid, is producing with a long length having slack, with the remainder of the wiring often being bundled and fixed to the body at multiple locations using adhesive tape or the like. However, since the wiring is rigid, a sense of discomfort is likely to arise at the time of wearing. In particular, wiring of a medical standard is often heavy and hard due to demands such as withstanding voltage, tensile strength, and suppression of impedance fluctuations, and so such wiring is likely to be subject to vibration and impart a great sense of discomfort when touching the skin.

In wearable biosignal acquisition devices such as belt-type and clothing-type wearable bioelectrodes, wiring such as a conductive thread or a metal wiring material is directly sewn or pasted on the fabric of the item, or accommodated in a storage space with a tunnel structure or a double structure provided in the item. However, since the wiring has poor elasticity and is rigid, the elasticity of the fabric is impaired at the portion where the wiring is attached, and the comfort becomes worse. In order to impart elasticity to the part where the wiring is attached, measures such as sewing the wiring in a zigzag shape may be taken. However, a sufficient effect is often not obtained, with the decrease in productivity and workability that results from such measures being a problem.

Also, with wearable biological signal acquisition devices, measurement of biological signals such as electrocardiograms and electromyograms becomes difficult if the wiring gets wet due to swimming, bathing, sweating, rain, or the like. Therefore, the wiring is also required to have excellent waterproofness.

Prior Art Documents

Non-Patent Documents

[Non-Patent Document 1] "Wearable sensors that have borne fruit across industry barriers—hitoe technology", NTT Technical Journal, vol. 26, no. 5, pp. 42-44, May 1, 2014.
[Non-Patent Document 2] "Wearable electronics and smart textiles: a critical review", Sensors, vol. 14, no. 7, pp. 11,957-11,992, 2014.

SUMMARY OF THE INVENTION

Problems to be Solved by the Invention

An object of the present invention is to provide an elastic wiring that is excellent in waterproofness and elasticity, hardly impairs elasticity of a fabric even when applied to a wearable item, and imparts negligible discomfort when worn.

Means for Solving the Problems

An elastic wiring according to an embodiment of the present invention includes an elastic tube, a conductor wire arranged within the tube, and fixing portions that fix the conductor wire and the tube at both ends of the tube in the lengthwise direction, wherein the length of the conductor wire between the fixing portions when the tube is in an unextended state is longer than the length of the tube between the fixing portions. In the elastic wiring according to one embodiment of the present invention, the fixing portions may each includes a caulking member, the caulking member may be provided with a male member and a female member, the male member being provided with a first flat plate portion and a fitting convex portion that is provided on the first flat plate portion, the female member being provided with a second flat plate portion and a fitting concave portion that is provided on the second flat plate portion, and the conductor wire and the tube may be caulked by the first flat plate portion and the second flat plate portion in a state of the fitting convex portion and the fitting concave portion being fitted together.

In the elastic wiring according to one embodiment of the present invention, a through hole may be formed in the fitting convex portion, and the conductor wire and the tube may be caulked by the male member and the female member in a state of a portion of the conductor wire exposed from an end portion of the tube being passed through the through hole, and a knot larger than the through hole being formed in the portion of the conductor wire that has passed through the through hole.

In the elastic wiring according to one embodiment of the present invention, the male member and the female member may be made of metal, and a protrusion may be formed in the female member.

In the elastic wiring according to one embodiment of the present invention, the fixing portions may each includes a caulking member, with the caulking member having a male member having a flat plate portion and a spike extending substantially perpendicularly from the flat plate portion, and a ring-shaped female member fixed to the male member by being crimped to the spike, wherein by fixing the female member to the male member, the conductor wire and the tube may be caulked by the flat plate portion and the female member, and a recess may be formed in the ring-shaped central portion of the female member.

In the elastic wiring according to one embodiment of the present invention, the conductor wire and the tube may be fixed by being stopped with a stopper.

In the elastic wiring according to one embodiment of the present invention, the conductor wire and the tube may be fixed by being bound with a band material.

A method for producing the elastic wiring according to one embodiment of the present invention passes the conductor wire through the tube, fixes the conductor wire and the tube at both ends of the tube in the lengthwise direction with the tube in an extended state, and returns the tube to the original state thereof.

Advantageous Effects of the Invention

The elastic wiring of the present invention has excellent waterproofness and elasticity, and even when applied to clothing, hardly impairs the elasticity of the fabric and has negligible discomfort when worn.

EMBODIMENTS FOR CARRYING OUT THE INVENTION

Hereinafter, an example of the elastic wiring according to the present invention will be described. The dimensions of the drawings illustrated in the following description are merely examples, with the present invention not necessarily being limited thereto and may be appropriately changed within a range that does not alter the gist of the present invention.

Figure 1:
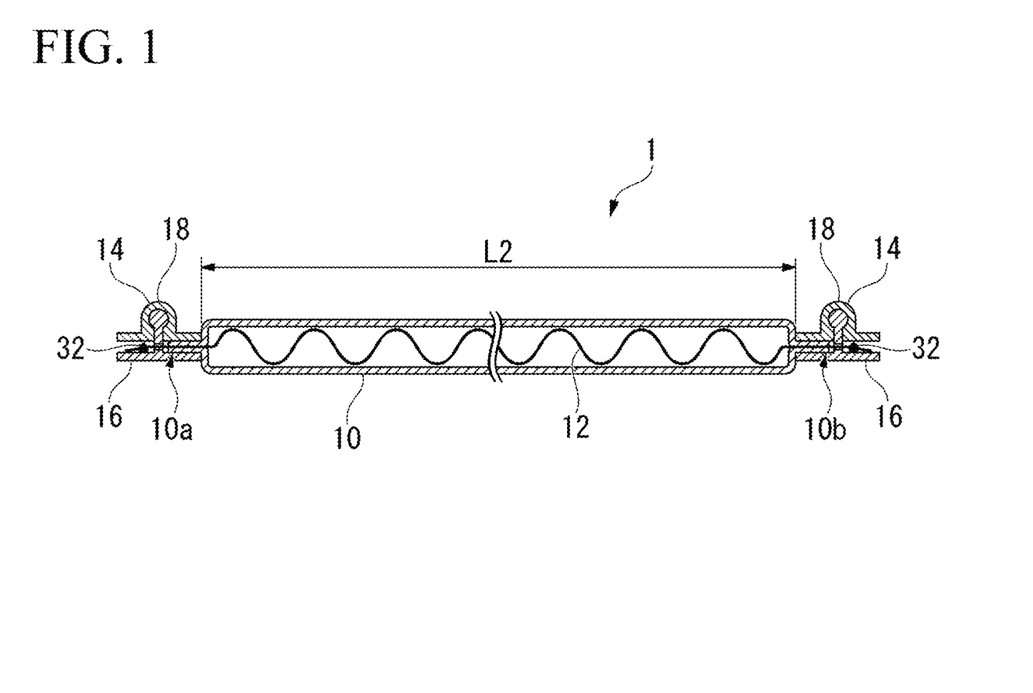
FIG. 1 is a cross-sectional view showing an elastic wiring according to an embodiment of the present invention.

An elastic wiring 1 according to the present embodiment is provided with a tube 10, a conductor wire 12, and a caulking member 14 as shown in FIG. 1.

The conductor wire 12 is arranged within the tube 10 so as to extend from a first end portion 10a to a second end portion 10b in the lengthwise direction of the tube 10. In the elastic wiring 1, the conductor wire 12 and the tube 10 are fixed by caulking by the caulking member 14 at both ends of the tube 10 in the lengthwise direction, namely, the first end portion 10a side and the second end portion 10b side.

The tube 10 has elasticity. That is, the tube 10 is a tube that hardly breaks when extended by application of a load in the lengthwise direction thereof, and has little residual displacement upon contracting when the load is removed. The elasticity of the tube 10 can be adjusted by the material and thickness of the tube 10.

As a material for forming the tube 10, an insulating material having elasticity can be used. For example, various elastomers such as silicone rubber, urethane rubber, natural rubber, isoprene rubber, butadiene rubber, styrene-butadiene rubber, chloroprene rubber, nitrile rubber, polyisobutylene, ethylene propylene rubber, chlorosulfonated polyethylene, acrylic rubber, fluorine rubber, and epichlorohydrin rubber can be used. As a material for forming the tube 10, silicone rubber is preferable from the viewpoint of heat resistance. As a material for forming the tube 10, one type may be used alone, or two or more types may be used in combination.

The extension at breakage of the tube 10 is preferably 25 to 300%, and more preferably 50 to 150%. If the extension at breakage of the tube 10 is equal to or greater than the lower limit of the above range, the elasticity of the elastic wiring 1 is improved and the sense of discomfort is further reduced. If the extension at breakage of the tube 10 is less than or equal to the upper limit of the above range, it is possible to avoid breakage and short circuiting of the wiring due to stress applied to the wiring as a result of stretching of the fabric when changing clothes.

The extension at breakage of the tube is measured according to JIS K-7127 (1999).

The inner diameter and the outer diameter of the tube 10 are not particularly limited, and may be set as appropriate so that the conductor wire 12 can be disposed in the tube 10. For example, the inner diameter of the tube 10 can be 0.1 to 10 mm, and the outer diameter can be 0.2 to 12 mm.

The thickness of the tube 10 is preferably 0.1 to 1 mm, and more preferably 0.2 to 0.6 mm. If the thickness of the tube 10 is equal to or greater than the lower limit of the above range, sufficient strength can be easily obtained.

If the thickness of the tube 10 is less than or equal to the upper limit of the above range, excellent elasticity is easily obtained.

As a material for forming the conductor wire 12, materials generally used for conductor wires can be used, and examples thereof include stainless steel (SUS), enamel, gold, platinum, and iridium. Among these, SUS is preferable as a material for forming the conductor wire 12 because it is not easily rusted, has excellent heat resistance, and can be washed when applied to clothing. The material for forming the conductor wire 12 may be one type or two or more types.

In the present invention, a combination of a tube formed of silicone rubber and a conductor wire formed of SUS yarn is particularly preferable.

The form of the conductor wire is not particularly limited, and for example may have the form of a single fiber or may have the form of a twisted thread in which a plurality of fibers are twisted together. In particular, the conductor wire 12 being in the form of interweaving strands is preferable from the standpoint of the conductor wire 12 having less of a tendency to spiral and become tangled in the tube 10 in an unextended state, and so can exist in a more stable state and allow smooth expansion and contraction of the elastic wiring 1.

The thickness of the conductor wire 12 can be set as appropriate, for example, 0.1 to 10 mm. Note that when the conductor wire 12 is a twisted thread composed of a plurality of wires, the outer diameter thereof is defined as the thickness of the conductor wire 12.

An insulating coat may be applied to the surface of the conductor wire 12. Since the surface of the conductor wire 12 is coated with insulation, the impedance change accompanying expansion and contraction is reduced. As the insulating material used for the insulating coating, publicly known materials can be used. For example, polyurethane, polyesterimide, polyamideimide, poiimide, PVC (polyvinyl chloride mixture), PE (polyethylene) fluororesin, TUFRET (tufflet), and rubber can be used. As a method of insulating coating, a publicly known method can be adopted.

The conductor wire 12 may be coated with a lubricant such as silicone oil or a rust preventive material.

In the elastic wiring 1, the conductor wire 12 is arranged and fixed in the tube 10 so that the length L1 of the conductor wire 12 between the fixing portions is longer than the length L2 of the tube 10 between the fixing portions when the tube 10 is not extended. That is, when the tube 10 is not extended, the conductor wire 12 is arranged and fixed in the tube so that the length L1 of the conductor wire 12 between the caulking members 14 and 14 is longer than the length L2 of the tube 10 between the caulking members 14 and 14.

Figure 3:
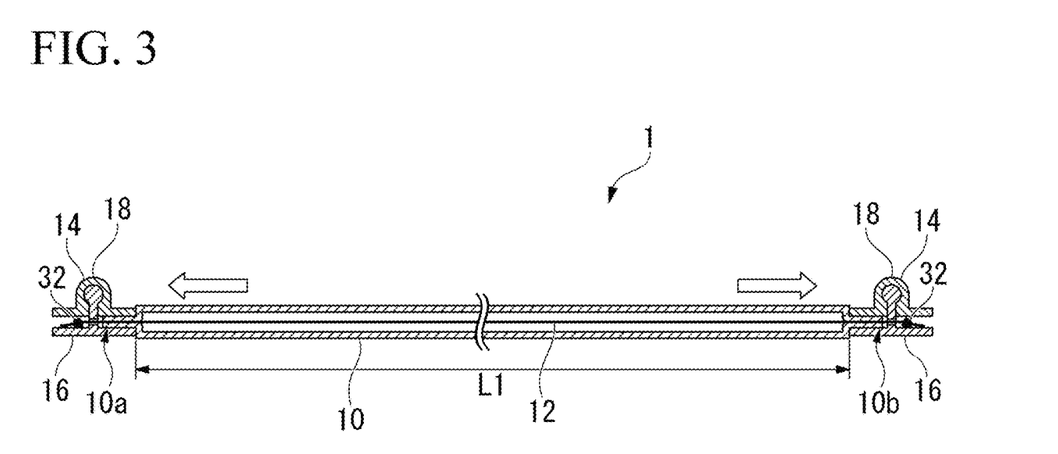
FIG. 3 is a cross-sectional view showing a state in which the elastic wiring of FIG. 1 is extended in the lengthwise direction thereof.

Note that when the tube 10 is extended by pulling in the lengthwise direction thereof, putting the conductor wire 12 in a state of being linearly tensioned as shown in FIG. 3, the length L1 of the conductor wire 12 between the fixing portions corresponds to the distance between the fixing portions by the connection members 40 at both ends.

Because the length L1 of the conductor wire 12 between the fixing portions is longer than the length L2 of the tube 10 between the fixing portions, the conductor wire 12 takes on a shape having curves or bends so as to have a spiral shape or a zigzag shape in the tube 10 when the tube 10 is not extended. Thus, even if the conductor wire 12 itself is not substantially elastic, the conductor wire 12 is not strained by curving or bending within the tube 10 and has slack allowing extension in the lengthwise direction thereof. Therefore, the elastic wiring 1 can be extended by being pulled until the conductor wire 12 becomes linear as shown in FIG. 3, and when the tensile load is released, the conductor wire 12 contracts due to the elasticity of the tube 10 as shown in FIG. 1.

Further, in the expansion and contraction of the elastic wiring 1, since the conductor wire 12 either has a shape with curves or bends or is linear, there is little impedance fluctuation of the conductor wire 12 accompanying the extension compared to a conductor wire including, for example, a conductive material mixed with an elastomer.

The ratio L1/L2 of the length L1 of the conductor wire 12 between the fixing portions to the length L2 of the tube 10 between the fixing portions in a state where the tube 10 is not extended is preferably 1.1 to 5, with 1.2 to 2 being more preferable. If the ratio L1/L2 is equal to or greater than the lower limit of the above range, excellent elasticity is easily obtained, and a sense of discomfort is further minimized. If the ratio L1/L2 is below the upper limit of the above range, production of the elastic wiring 1 will be easy and productivity will become high.

The periphery of the conductor wire 12 in the tube 10 may be in a state in which air is present or in a state in which a liquid is filled therein. A state in which is air present is preferable from the standpoint of ease of production of the elastic wiring 1.

The liquid to be filled around the conductor wire 12 in the tube 10 may be any liquid that does not inhibit movement of the conductor wire 12 within the tube 10 and that does not degrade the conductor wire 12, with examples including oil-based oil, silicone oil, glycerin, glycerol and the like.

Figure 2:
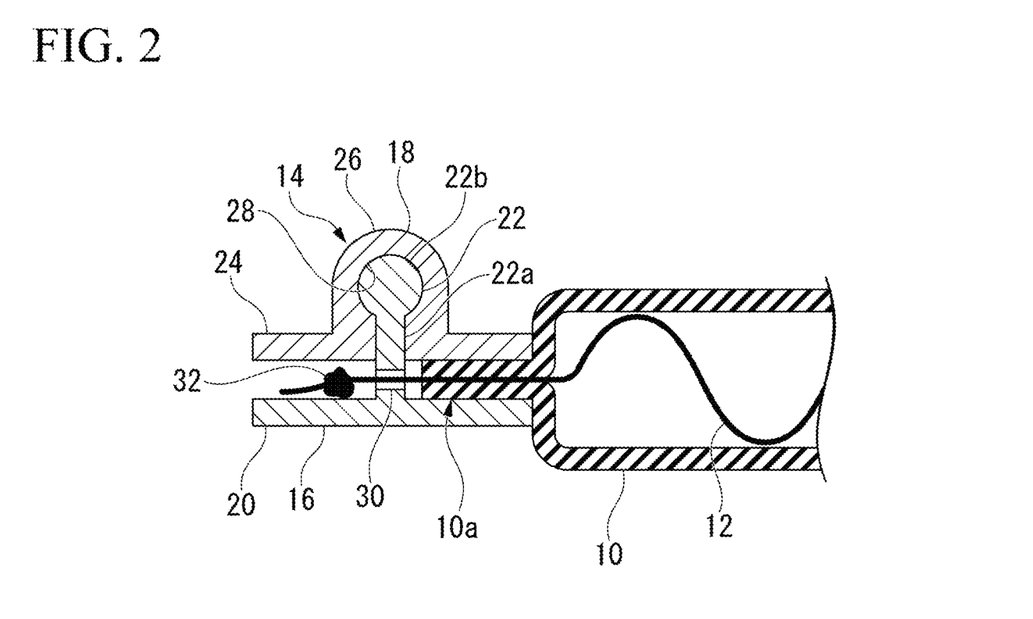
FIG. 2 is an enlarged cross-sectional view showing an end portion in the lengthwise direction of the elastic wiring in FIG. 1.

As shown in FIGS. 1 and 2, the caulking member 14 is provided with a male member 16 and a female member 18.

The male member 16 is provided with a disk-shaped first flat plate portion 20 and a fitting convex portion 22 provided so as to rise from the central portion of the first flat plate portion 20. The fitting convex portion 22 is provided with a trunk portion 22a that rises from the first flat plate portion 20, and a spherical head portion 22b that is provided at the tip of the trunk portion 22a.

The female member 18 is provided with a disk-shaped second flat plate portion 24 and a protrusion 26 provided at the center of the second flat plate portion 24, with a fitting concave portion 28 being formed in the protrusion 26. The fitting concave portion 28 opens at the lower surface of the second flat plate portion 24. The fitting concave portion 28 of the female member 18 is adapted to fit the head portion 22b of the fitting convex portion 22 of the male member 16.

In this way, the male member 16 and the female member 18 are configured such that the fitting convex portion 22 and the fitting concave portion 28 are detachably fitted.

At both end portions in the lengthwise direction of the tube 10, the tube 10 and the conductor wire 12 are caulked and fixed by the fitting convex portion 22 and the fitting concave portion 28 being fitted together so that the tube 10 and the conductor wire 12 are sandwiched by the first flat plate portion 20 of the male member 16 and the second flat plate portion 24 of the female member 18.

In the present invention, it is preferable that the conductor wire and the tube be caulked and fixed by the caulking member as in this example, since the tube and the conductor wire can be easily and firmly fixed at the fixing portions at both ends of the tube. Moreover, it is more preferable that the conductor wire and the tube be caulked by the first flat plate portion of the male member and the second flat plate portion in a state where the male member and the female member of the caulking member are fitted together.

In this example, a through hole 30 is formed in the trunk portion 22a of the fitting convex portion 22 of the male member 16. At the first end portion 10a side of the tube 10, a portion of the conductor wire 12 exposed from the tube 10 is passed through the through hole 30, and a knot 32 larger than the through hole 30 is formed on the distal side of the conductor wire 12 that has passed through the through hole 30. In this state, the conductor wire 12 and the tube 10 are caulked by the male member 16 and the female member 18. Similarly, at the second end portion 10b side of the tube 10, a portion of the conductor wire 12 exposed from the tube 10 is passed through the through hole 30 and the knot 32 is formed. In this state, the conductor wire 12 and the tube 10 are caulked by the male member 16 and the female member 18.

In this way, in the present invention, it is preferable to caulk the conductor wire and the tube in a state of the portion of the conductor wire exposed from the end of the tube being passed through the through hole of the caulking member, and a knot larger than the through hole being formed at the portion of the conductor wire that has passed through the through hole.

By passing the distal end side of the conductor wire 12 through the through hole 30 of the fitting convex portion 22 and forming the knot 32 thereon as in this embodiment, it is possible to prevent unexpected pullout of the conductor wire 12 when fixing the conductor wire 12 and the tube 10, and stably arrange the conductor wire 12 between the male member 16 and the female member 18. Therefore, the conductor wire 12 and the tube 10 can be more easily fixed by the caulking member 14, leading to an improved yield.

The material for forming the caulking member 14 is not particularly limited, and examples thereof include stainless steel (SUS), brass, copper, iron, silver, gold, platinum, aluminum, and tin. By forming the caulking member 14 with metal, it is possible to use the caulking member 14 as a male connector that electrically connects to other members.

As the caulking member 14, for example, a snap button can be adopted.

A method for producing the elastic wiring 1 includes the following method.

Figure 4A:
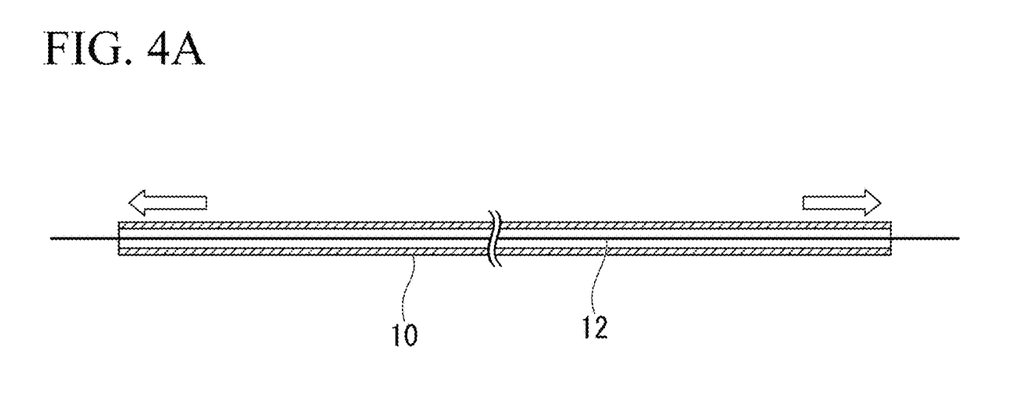
FIG. 4A is a cross-sectional view showing a production process of the elastic wiring shown in FIG. 1.
Figure 4B:
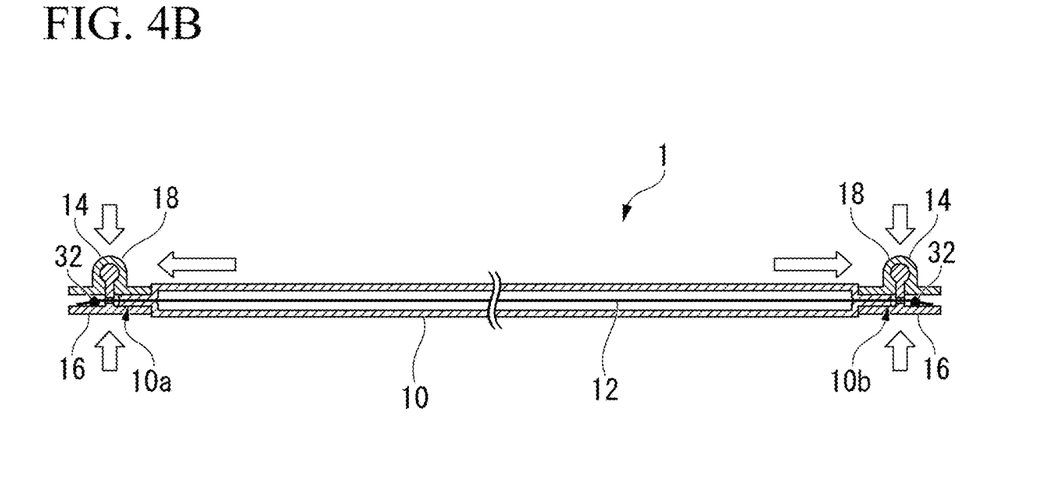
FIG. 4B is a cross-sectional view showing a production process of the elastic wiring shown in FIG. 1.
Figure 4C:
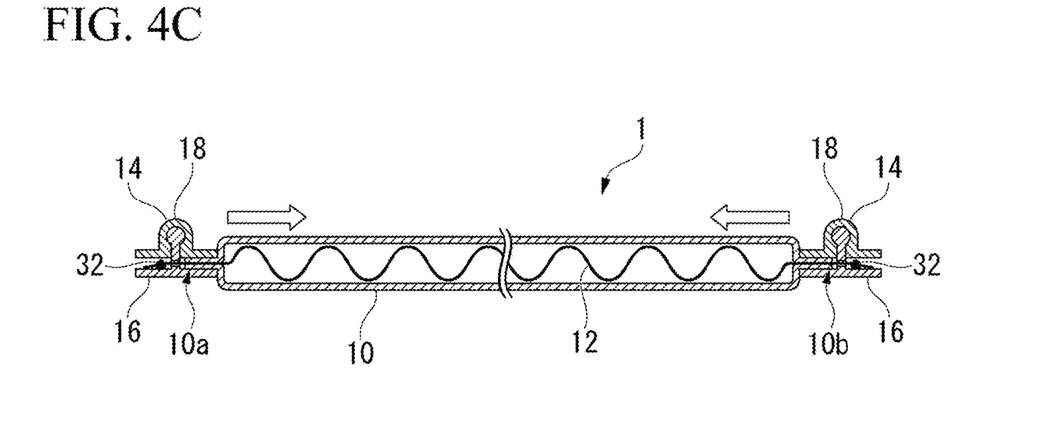
FIG. 4C is a cross-sectional view showing a production process of the elastic wiring in FIG. 1.

As shown in FIG. 4A, the conductor wire 12 is passed through the tube 10 and loads pulling in the lengthwise direction are applied to the tube 10 so put the tube 10 in an extended state. In this state, as shown in FIG. 4B, the conductor wire 12 and the tube 10 are caulked and fixed by the caulking members 14 at both end portions in the lengthwise direction of the tube 10. Thereafter, as shown in FIG. 4C, by releasing the loads pulling the tube 10 and returning the tube 10 to the original unextended state, the elastic wiring 1 is obtained.

More specifically, an example will be described in which a silicon tube having an outer diameter of 2 mm and a wall thickness of about 0.2 mm is used as the tube 10 and a SUS (Steel Use Stainless) wire having a length of about 140 cm is used as the conductor wire 12. The thickness of the SUS wire (SUS304) is 12µm and the mass is 0.22 g/m. The SUS wire is covered with the silicon tube, both ends of the silicon tube and the SUS wire are fixed, and the length of the tube and the SUS wire are contracted about 50%.

The elastic wiring 1 obtained in this way had a wire diameter of 2.5 mm and a length of 60 cm in a state of tension not being applied. When the elastic wiring 1 was tensioned in the lengthwise direction to be fully extended, the length became 136 cm. The tension (initial motion sensitivity) when this elastic wiring 1 starts to be extended was 0.03 Newton (N), and the tension required for complete extension (maximum tension at the time of extension) was 1.2 N. The DC resistance value of the SUS wire of the elastic wiring 1 was 30.5Ω, and no change in the resistance value due to the extension was observed. When the elastic wiring 1 was completely extended and then the tension was released, the wire diameter was 2.5 mm and the length returned to 60 cm.

As described above, the elastic wiring 1 can be extended with a small tension. Accordingly, when worn by the subject together with clothes, the elastic wiring 1 is extended without a sense of discomfort like a rubber string. Upon extension with movement of the body when used as a wearable wiring, the elastic wiring 1 does not exert tension on a connected bioelectrode. Therefore, there is no shifting of the bioelectrode from the mounted position, and distortion of the signal obtained from the bioelectrode hardly occurs.

The wire diameter of this elastic wiring 1 is 2.5 mm, which is thinner than conventional cables. Moreover, by using the silicon tube as the tube, this elastic wiring 1 is flexible and soft to the touch. The elastic wiring 1 is attached to clothing and, even when in direct contact with skin, does not produce discomfort so is suitable for long-term biomedical measurement. The elastic wiring 1 using silicon and SUS wire is resistant to heat and chemicals, can be washed with a washing machine, and can be dried with a drying machine or a dryer.

When forming the knot 32 on the first end 10a side and the second end 10b side of the tube 10 by passing the portion exposed from the tube 10 of the conductor wire 12 through the through hole 30 in the manner of the elastic wiring 1 of the present embodiment, the operation may be performed with the tube 10 extended, or may be performed before the tube 10 is extended.

As methods for producing the tube 10 and the conductor wire 12, publicly known methods can be used.

As described above, in the present invention, a conductor wire is arranged in an elastic tube, and the conductor wire and the tube are fixed at both ends of the tube so that the length of the conductor wire between the fixing portions in a state where the tube is not extended is longer than the length of the tube between the fixing portions. Thereby, in the state in which the elastic wiring of the present invention is not extended, since the conductor wire exists in a shape with slack having curves and bends within the tube, excellent elasticity is obtained.

The elastic wiring of the present invention is not limited to the elastic wiring 1 described above.

For example, the mode of fixing the tube and the conductor wire in the elastic wiring of the present invention is not limited to a mode using the caulking member 14. The elastic wiring of the present invention may be one in which the tube and the conductor wire are caulked and fixed by a caulking member in which the through hole 30 is not formed in the male member 16 of the caulking member 14.

The elastic wiring of the present invention may be one in which the conductor wire and the tube are fixed by being stopped with a stopper. Specifically, for example, an elastic wiring 2 illustrated in FIG. 5 may be used.

Figure 5:
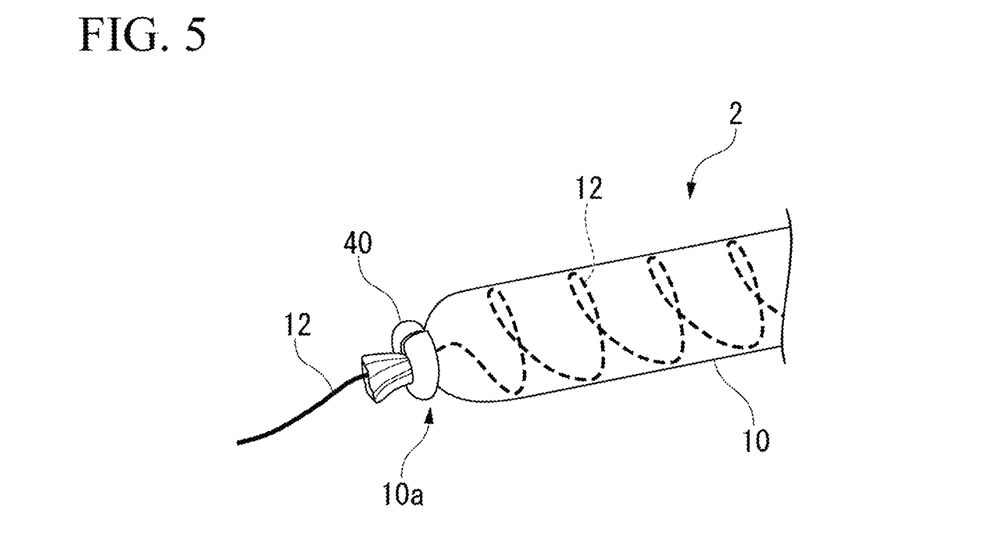
FIG. 5 is a perspective view showing an elastic wiring according to another embodiment of the present invention.

The elastic wiring 2 has the same mode as the elastic wiring 1 except that the tube 10 and the conductor wire 12 are fixed by a stopper 40 instead of being fixed by the caulking member 14.

The stopper 40 is a rod-like fitting, being deformed into an annular shape so as to stop the conductor wire 12 and the tube 10 at a portion on the first end portion 10a side in the lengthwise direction of the tube 10. As described above, in the elastic wiring 2, the conductor wire 12 and the tube 10 are fixed by being stopped with the stopper 40 at the portion on the first end portion 10a side in the lengthwise direction of the tube 10. At the second end portion 10b side as well of the tube 10 in the lengthwise direction, the conductor wire 12 and the tube 10 are fixed by being stopped with the stopper 40.

Examples of the metal constituting the stopper 40 include SUS, brass, iron, and aluminum. The metal constituting the stopper 40 may be one type or two or more types.

The length and thickness of the stopper 40 may be set as appropriate as long as the conductor wire 12 and the tube 10 can be firmly fixed.

The elastic wiring of the present invention may be one in which the conductor wire and the tube are fixed by being bound with a band material. Specifically, for example, an elastic wiring 3 illustrated in FIG. 6 may be used.

Figure 6:
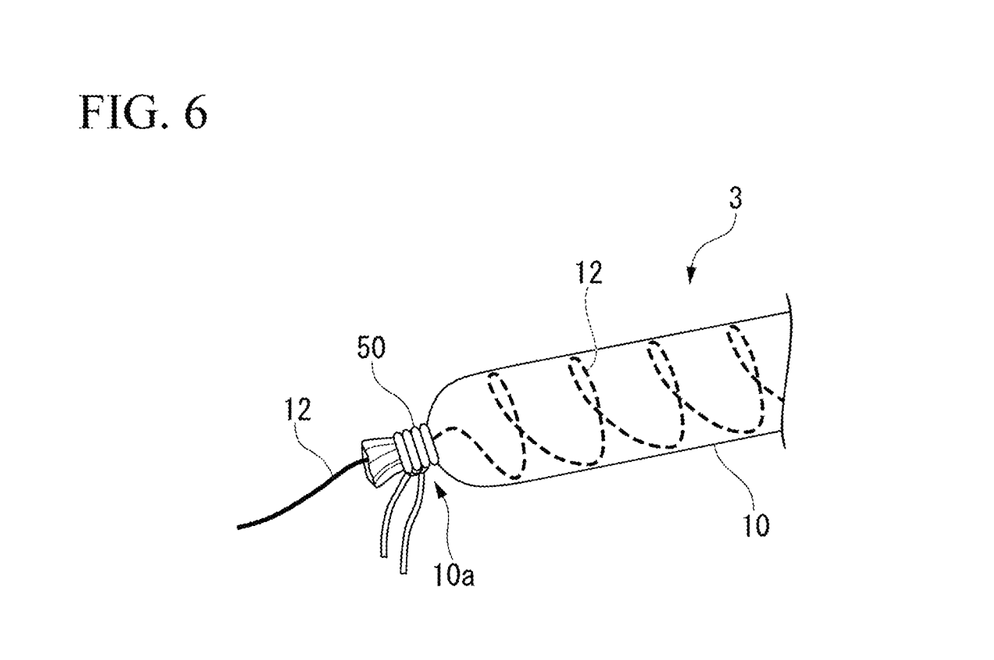
FIG. 6 is a perspective view showing an elastic wiring according to still another embodiment of the present invention.

The elastic wiring 3 has the same mode as the elastic wiring 1 except that the tube 10 and the conductor wire 12 are fixed by a band material 50 instead of being fixed by the caulking member 14.

In the elastic wiring 3, the conductor wire 12 and the tube 10 are bound together and fixed by the band material 50 being wound and tied on a portion of the tube 10 on the first end portion 10a side thereof in the lengthwise direction. In addition, the conductor wire 12 and the tube 10 are bound together and fixed by the band material 50 being wound and tied on a portion of the tube 10 on the second end portion 10b side thereof in the lengthwise direction.

As the form of the band material 50, any material can be used provided the band material 50 can bind and fix the conductor wire and the tube, and examples thereof include a binding band and a string. As the band material 50, one type may be used independently or two or more types may be used together.

The material for forming the band member 50 is not particularly limited, and examples thereof include polyethylene, polyethylene terephthalate, polyurethane, polystyrene, nylon, polycarbonate, fluorine resin, silicone rubber, and metals such as SUS, brass, iron, and aluminum.

The length and thickness of the band member 50 may be set as appropriate as long as the conductor wire 12 and the tube 10 can be firmly fixed.

The elastic wiring of the present invention may be one in which a tube and a conductor wire are fixed by crimping using a crimping terminal. The crimping terminal may be any one capable of fixing the tube and the conductor wire by crimping, and a publicly known crimping terminal usually used for wiring can be employed.

Figure 7:
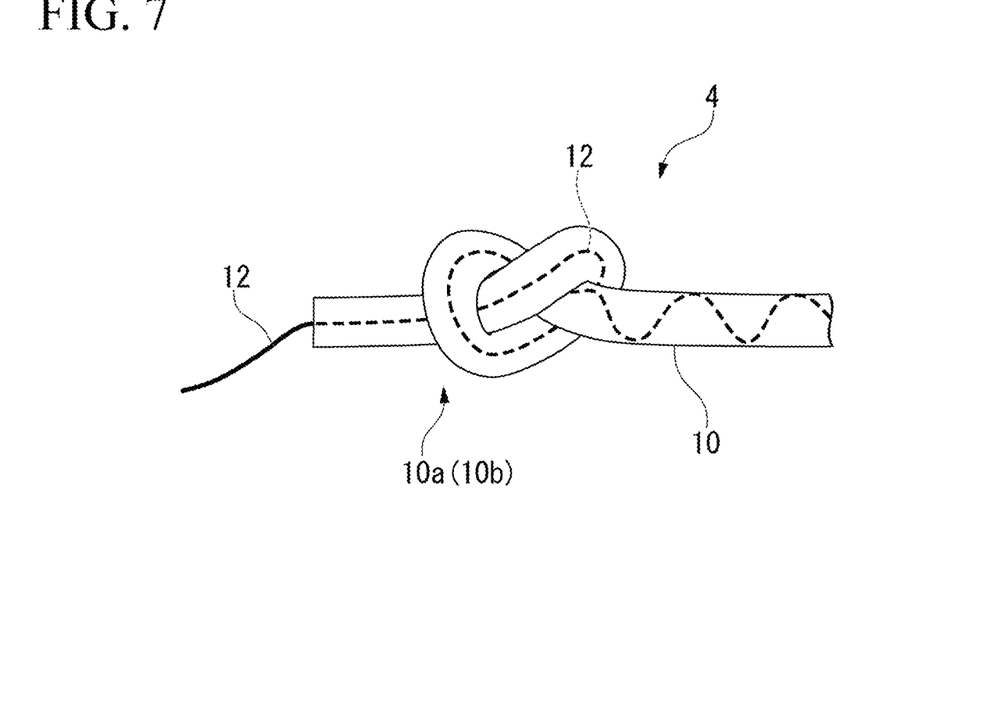
FIG. 7 is a side view showing an elastic wiring according to yet still another embodiment of the present invention.

The elastic wiring of the present invention may be an elastic wiring 4 in which, as shown in FIG. 7, the tube 10 and the conductor wire 12 are fixed by portions of the tube 10 on the first end portion 10a side and the second end portion 10b side in the lengthwise direction thereof being respectively knotted together with the conductor wire 12.

The elastic wiring of the present invention may also be an elastic wiring in which the tube and the conductor wire are fixed by a pin terminal being inserted into both ends of the tube in the lengthwise direction thereof, with the portions of the tube in which the pin terminal has been inserted being bound with a string. The pin terminal is not particularly limited, and a publicly known crimping terminal normally used for wiring can be used.

As described above, the caulking member 14 of the elastic wiring 1 shown in FIG. 2 can be used as the male connector. As will be described below, in another embodiment, the caulking member can also be used as the female connector.

Figure 8:
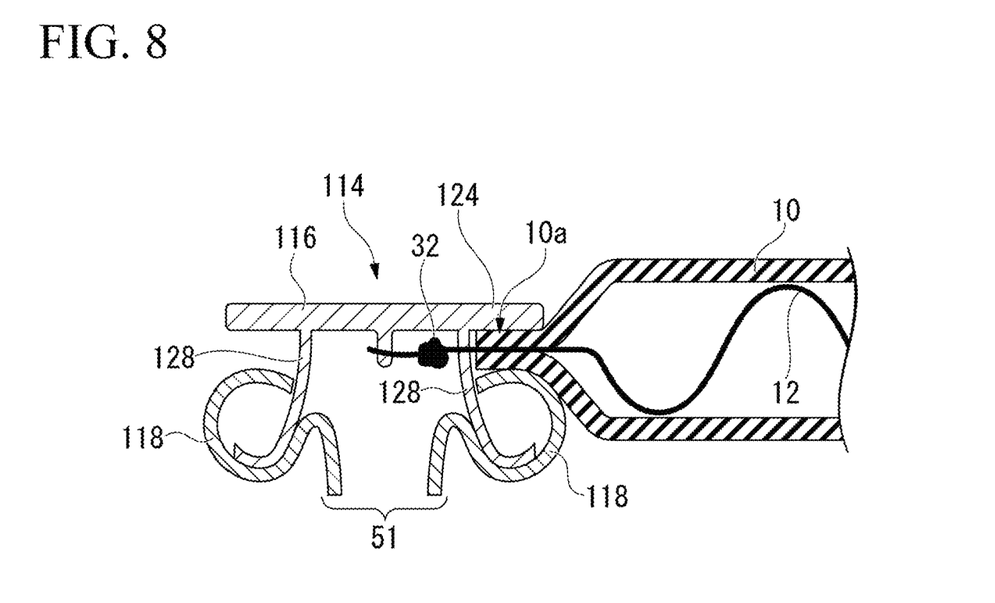
FIG. 8 is a cross-sectional view showing an elastic wiring according to even yet still another embodiment of the present invention.

That is, referring to FIG. 8, a caulking member 114 includes a ring-shaped male member 116 and a ring-shaped female member 118. The female member 118, which has a spring property, is fixed to the ring-shaped male member 116 by being crimped to a spike 128 formed on the male member 116. The ring-shaped male member 116 has a ring-shaped flat plate portion 124. The spike 128 is formed so as to extend substantially perpendicularly to the flat plate portion 124. The female member 118 is caulked against the male member 116, thereby pressing the end portion 10a of the tube 10 sandwiched between the flat plate portion 124 and female member 118 onto the flat plate portion 124. That is, the female member 118 presses the end portion 10a of the tube 10 against the flat portion 124 by the spring force of the spike 128 and the female member 116. Thereby, the tube 10 and the conductor wire 12 are fixed by the female member 118 and the flat plate portion 124.

The knot 32 is formed on the conductor wire 12 drawn from the tube 10. The knot 32 is arranged at the center of the ring-shaped male member 116 with respect to the spike 123 to prevent the conductor wire 12 and the tube 10 from coming off the male member 116.

The ring-shaped female member 118 and the ring-shaped male member 116 are made of metal. Therefore, with the above configuration, the conductor wire 12 is electrically connected to the female member 118 via the male member 116. The female member 118 has a recess 51 at the center. This recess 51 is engaged with the protrusion 26 of the male connector shown in FIG. 2, thereby electrically connecting the male connector shown in FIG. 2 and the female connector shown in FIG. 8.

In the present invention, two or more of the above-described modes may be combined as a mode for fixing the tube and the conductor wire.

In the present invention, from the viewpoint of having excellent industrial productivity, a mode that caulks and fixes the tube and the conductor wire with the caulking member provided with the male member and female member such as the caulking member 14 is preferable among the above-described modes.

Further, in the elastic wiring of the present invention, the tube and the conductor wire may be fixed not only at both ends of the tube but also at portions other than both ends in the lengthwise direction of the tube. That is, the number of fixing portions at which the tube and the conductor wire in the elastic wiring of the present invention are fixed is not limited to two, and may be three or more.

As described above, in the present invention, a conductor wire is arranged in an elastic tube, and the conductor wire and the tube are fixed at both ends of the tube so that the length of the conductor wire between the fixing portions in a state where the tube is not extended is longer than the length of the tube between the fixing portions. Thereby, in the state in which the elastic wiring of the present invention is not extended, since the conductor wire exists in a shape with slack having curves and bends within the tube, excellent elasticity is obtained.

The elastic wiring of the present invention, by having excellent elasticity as described above, is particularly suitable to wearable bio-signal acquisition devices. For example, by applying the elastic wiring of the present invention to a garment-type bio-signal acquisition device such as underwear, the elasticity of the knitted fabric is hardly impaired when being put on or taken off, and a sense of discomfort can be reduced. In addition, when a garment to which the elastic wiring of the present invention is applied is worn, the elastic wiring is in a contracted state resembling a rubber string passed through the garment, and so by being stored in a state fitted to the fabric, there is little discomfort.

Also, the elastic wiring of the present invention is excellent in waterproofness because the conductor wire is accommodated in the tube.

Figure 9:
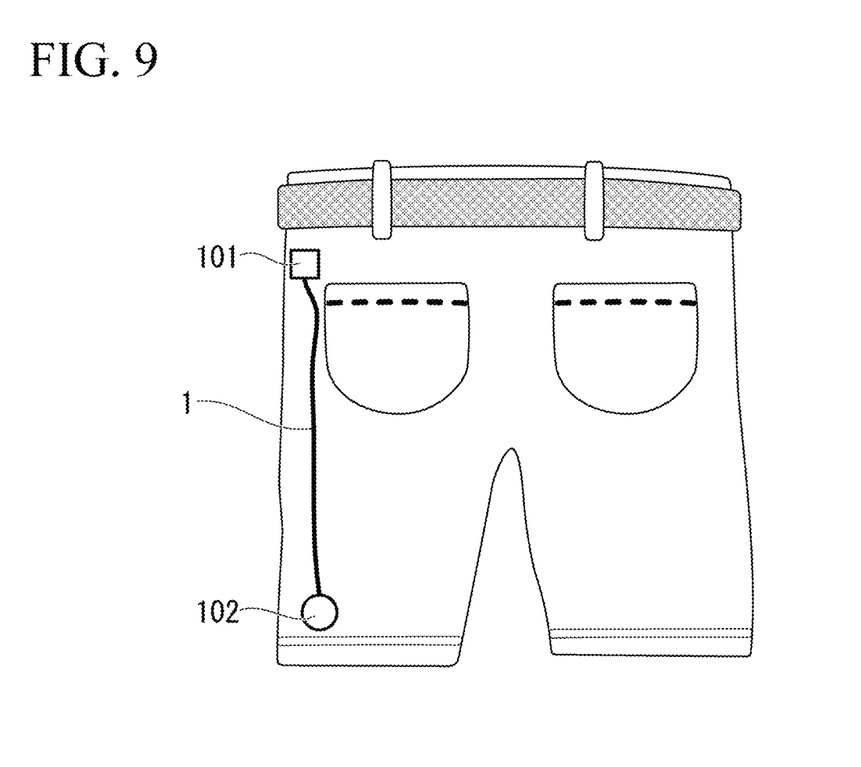
FIG. 9 is a front view showing a garment equipped with the elastic wiring of one embodiment of the present invention.

FIG. 9 is a schematic view of the elastic wiring 1 being fixed to a garment. Both ends of the elastic wiring 1 connect a transmitter 101 and a sensor 102, respectively.

Here, in addition to the trousers shown in FIG. 9, the garment may be of any type such as a muffler, bandage, and socks, as long as the wiring of the present invention can be fixed thereto, and any method of fixing the wiring may be used. In addition, as the sensor 102, any sensor may be chosen as appropriate, such as a wearable electrode, a pulse sensor, a thermometer, and an accelerometer, and the number and types of sensors may be a plurality.

For example, when using a pulse sensor, the pulse data measured by the sensor 102 can be transferred to the outside by the transmitter 101. While the wiring 1 may be arranged either on the inside or outside of the garment, if arranged on the inside, the wiring is not visible, and so the garment can be used as smart wear that acquires biometric data without the wearer being aware of the wiring.

The fixing method and fixing position of the transmitter 101 and the sensor 102 may be arbitrarily determined. For example, fixing to different garment is possible, in which the transmitter 101 is fixed to trousers and the sensor 102 is fixed to socks.

Further, in the elastic wiring of the present invention, it is possible to wash the wear to which the elastic wiring is applied by using SUS yarn as the conductor wire. In addition, since elastic wiring using a tube made of silicone rubber is excellent in heat resistance and chemical resistance, clothing to which the elastic wiring is applied can be used in harsh environments as fire-resistant, incombustible and chemical resistant wear.

Description of the Reference Symbols

1~4: Elastic wiring
10: Tube
10a: First end portion
10b: Second end portion
12: Conductor wire
14: Caulking member
16: Male member
18: Female member
20: First flat plate portion
22: Fitting convex portion
22a: Trunk portion
22b: Head portion
24: Second flat plate portion
26: Protrusion
28: Fitting convex portion
30: Through hole
32: Knot
40: Stopper
50: Band material

The invention claimed is:

1. A method for producing an elastic wiring comprising an elastic tube; a conductor wire arranged within the tube; and caulking members that fix the conductor wire and the tube at both ends of the tube in the lengthwise direction, wherein:
   a length of the conductor wire between the fixing portions when the tube is in an unextended state is longer than a length of the tube between the fixing portions;
   each of the caulking members includes a male member and a female member; the male member comprises a first flat plate portion and a fitting convex portion that is provided on the first flat plate portion; and
   the female member comprises a second flat plate portion and a fitting concave portion that is provided on the second flat plate portion,
the method comprising:
   passing the conductor wire through the tube, fixing the conductor wire and the tube at both ends of the tube in the lengthwise direction with the tube in an extended state, and returning the tube to the original state thereof; and
caulking the conductor wire and the tube by the first flat plate portion and the second flat plate portion in a state of the fitting convex portion and the fitting concave portion being fitted together.

2. A method for producing an elastic wiring comprising an elastic tube; a conductor wire arranged within the tube; and caulking members that fix the conductor wire and the tube at both ends of the tube in the lengthwise direction, wherein:
   a length of the conductor wire between the fixing portions when the tube is in an unextended state is longer than a length of the tube between the fixing portions; and
   each of the caulking members includes a male member comprising a flat plate portion and a spike extending substantially perpendicularly from the flat plate portion, and a ring-shaped female member fixed to the male member by being crimped to the spike;
   the method comprising:
   passing the conductor wire through the tube, fixing the conductor wire and the tube at both ends of the tube in the lengthwise direction with the tube in an extended state, and returning the tube to the original state thereof; and
   by fixing the female member to the spike of the male member, caulking the conductor wire and the tube by the flat plate portion and the female member so as to form a recess in the ring-shaped central portion of the female member.

* * * * *